(12) United States Patent
Nguyen et al.

(10) Patent No.: US 8,496,652 B2
(45) Date of Patent: Jul. 30, 2013

(54) BALLOON CATHETER SYSTEMS AND METHODS FOR TREATING UTERINE DISORDERS

(75) Inventors: Steven Nguyen, North Brunswick, NJ (US); Vaclav O. Podany, New Fairfield, CT (US)

(73) Assignee: Ethicon, Inc., Somerville, NJ (US)

( * ) Notice: Subject to any disclaimer, the term of this patent is extended or adjusted under 35 U.S.C. 154(b) by 1015 days.

(21) Appl. No.: 12/134,265

(22) Filed: Jun. 6, 2008

(65) Prior Publication Data

US 2009/0306588 A1    Dec. 10, 2009

(51) Int. Cl.
*A61B 18/08* (2006.01)

(52) U.S. Cl.
USPC ............................................................ 606/28

(58) Field of Classification Search
USPC ...................................... 606/28, 41
See application file for complete search history.

(56) References Cited

U.S. PATENT DOCUMENTS

| 4,949,718 | A |   | 8/1990 | Neuwirth et al. |
| 5,462,545 | A | * | 10/1995 | Wang et al. ....................... 606/41 |
| 5,571,153 | A |   | 11/1996 | Wallsten |
| 5,653,692 | A |   | 8/1997 | Masterson et al. |
| 5,800,493 | A |   | 9/1998 | Stevens et al. |
| 5,891,094 | A |   | 4/1999 | Masterson et al. |
| 5,935,105 | A |   | 8/1999 | Manning et al. |
| 5,954,714 | A |   | 9/1999 | Saadat et al. |
| 6,187,346 | B1 |   | 2/2001 | Neuwirth |
| 6,944,394 | B2 |   | 9/2005 | Long et al. |
| 6,960,203 | B2 | * | 11/2005 | Xiao et al. ....................... 606/27 |
| 2004/0002698 | A1 |   | 1/2004 | Hua Xiao et al. |

FOREIGN PATENT DOCUMENTS

WO   WO 98/22032 A1   5/1998
WO   WO 00/00100 A1   1/2000

* cited by examiner

*Primary Examiner* — Michael Peffley
*Assistant Examiner* — Daniel Fowler

(57) ABSTRACT

A system for treating uterine disorders includes a balloon catheter having a cannula with a proximal end and a distal end, and an inflatable balloon secured over the distal end of the cannula. The device includes a heating assembly coupled with the distal end of the cannula and disposed inside the inflatable balloon, and an impeller disposed inside the heating assembly. In one embodiment, the heating assembly includes an elongated heating tube having a heating film covering an outer wall thereof, at least one fluid inlet extending though the outer wall and a fluid outlet located at a distal end of the elongated heating tube. The impeller is rotatable for drawing fluid through the at least one fluid inlet and into the elongated heating tube for heating the fluid, and discharging the heated fluid from the fluid outlet for circulating the fluid throughout the inflatable balloon.

20 Claims, 14 Drawing Sheets

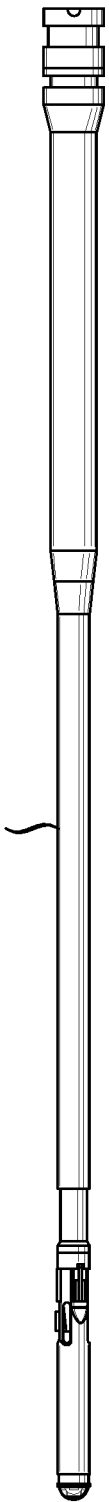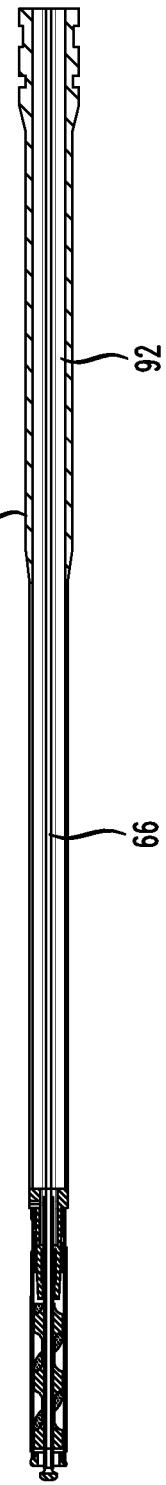

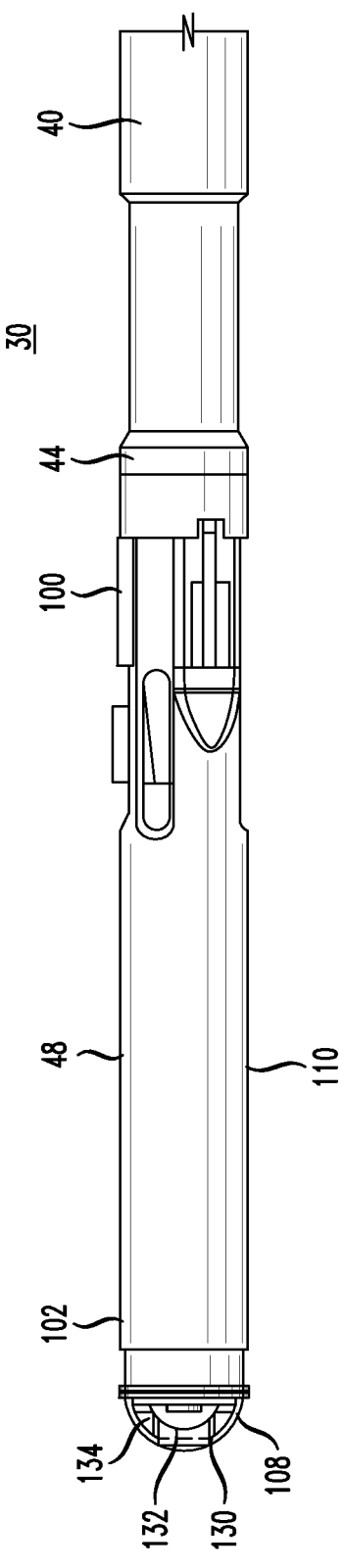
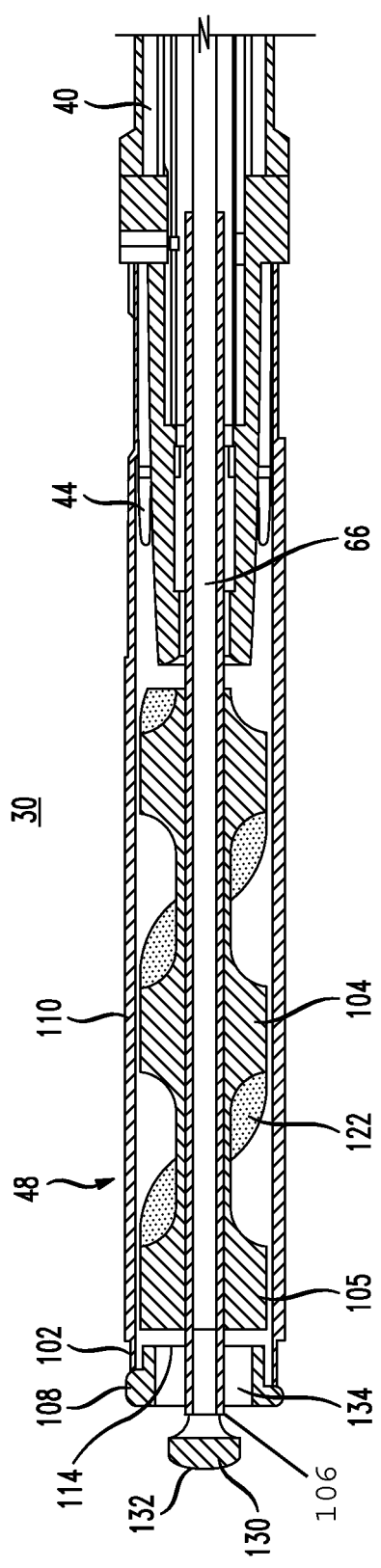
FIG. 7A
FIG. 7B

BALLOON CATHETER SYSTEMS AND METHODS FOR TREATING UTERINE DISORDERS

BACKGROUND OF THE INVENTION

1. Field of the Invention

The present application is generally related to treating uterine disorders and is more specifically related to systems and methods using balloon catheters for treating uterine disorders.

2. Description of the Related Art

Excessive or abnormal uterine bleeding in premenopausal females, commonly referred to as menorrhagia, has been a leading cause of about 30% of the hysterectomies performed in the United States. Women afflicted with menorrhagia typically lose 10 to 25 times the normal amount of blood during their menstrual cycle and often contend with iron deficiencies, pain, fatigue, and the inability to participate in daily activities. While hysterectomies are effective, less invasive outpatient procedures have been introduced that preserve the uterus and reduce recovery time. One of the newer procedures, commonly referred to as endometrial ablation, involves inserting a balloon filled with a heated fluid into the uterus. In one embodiment of a system sold under the trademark THERMACHOICE by Johnson & Johnson of New Brunswick, N.J., a balloon catheter is inserted into a uterus, and inflated with a 5% dextrose solution. After the balloon is inflated with the solution to a certain pressure, the fluid is heated to a predetermined temperature for a period of time that coagulates, ablates, necroses, or destroys the endometrium layer of the uterus. After the procedure is completed, the fluid is withdrawn from the balloon and the balloon is removed from the uterus. The uterine lining will then shed over a 7-10 day period.

An endometrial ablation procedure requires controlling the temperature and internal temperature of the balloon. Temperature fluctuations and gradients along the surface of the balloon may cause uneven tissue ablation resulting in a less than optimal outcome. Balloon surface temperature fluctuations and gradients are the result of the fluid not mixing fully within the balloon. When the fluid is not completely mixed, the fluid temperature is subject to convection currents of the fluid within the balloon. While cooler fluid moves toward the bottom of the balloon, the warmer, less dense fluid rises. When the fluid within the balloon is subject to such convection during heating, considerable temperature fluctuations along the surface of the balloon may result.

Some balloon catheters circulate fluid by means of separate inlet and outlet passages that connect the balloon with an external heating element. Heat is circulated from the external heating element through the inlet passage into the balloon. Then, the fluid from the balloon is returned to the external heating element through the outlet passage. Such a balloon catheter design requires the hot fluid to pass through the vagina and the opening of the cervix, which may cause physical discomfort or possible tissue damage as heat is conducted through the balloon catheter walls. Since the hot fluid must travel a significant distance between the external heating element and the balloon surface being heated, efficient control over the temperature of the balloon surface is difficult.

Other known heated balloon catheters circulate fluid via a pair of one way valves mounted within a housing located at the end of a fluid delivery tube. The housing is surrounded by an inflatable member, such as a balloon. The first valve permits fluid flow from the housing into the balloon, and the second valve permits flow from the balloon into the housing. The valves respond to alternating pressure differentials between the balloon and the housing created by an external bellows or piston which causes pulses of fluid to move up and down the fluid delivery tube. Such a configuration requires circulating hot fluid from the balloon into the fluid delivery tube, creating a risk of causing discomfort to the patient or vaginal tissue damage.

Mechanical circulation or agitation of fluid within the balloon has been known to improve temperature consistency over the surface of the balloon. For example, commonly assigned U.S. Pat. No. 5,954,714, the disclosure of which is hereby incorporated by reference herein, teaches a device for endometrial ablation procedures including a balloon having an internal heater for heating a fluid to a desired temperature. A rotary impeller is positioned distally of the heater for causing the fluid inside the balloon to move around the balloon. The circulation of the fluid by the rotary impeller eliminates some of the temperature differentials along the surface of the balloon, particularly those portions of the balloon proximate the cornua region of the uterus.

Commonly assigned U.S. Pat. No. 5,891,094, the disclosure of which is hereby incorporated by reference herein, teaches a system for the direct heating of a fluid solution in a hollow body organ. The system includes a distal tip having fluid inflow lumens that direct the fluid into a heating chamber. An impeller is located distally of the heating chamber. As fluid enters the heating chamber from the inflow lumens, it passes by electrodes for heating the fluid and exits the chamber through outlets. The impeller rotates for pulling the fluid into the heating chamber and then discharging the fluid through the outlet for circulation within the uterine cavity.

In spite of the above advances, there remains a need for balloon catheter systems and methods that more accurately and efficiently heat the fluid inside the balloon, that more efficiently monitor and control fluid pressure inside the balloon, that more efficiently circulate fluid throughout the balloon, that more efficiently transfer heat from a heating element to fluid, and that provide more uniform heating of the balloon surface.

SUMMARY OF THE INVENTION

As used herein, the terminology "menorrhagia" means a condition of excessive menstrual bleeding in women; "thermal coagulation" means the application of heat to tissue in an amount sufficient to destroy the tissue; "necrosis" means the death of cells in tissue; and "endometrium" is the mucous membrane lining of the inner surface of the uterus that grows during each menstrual cycle and is shed in menstrual blood.

In one embodiment of the present invention, a system for treating uterine disorders, such as a system for conducting endometrial ablation procedures, includes a balloon catheter having a cannula with a proximal end and a distal end. The system includes an inflatable balloon secured over the distal end of the cannula, a heating assembly coupled with the distal end of the cannula and disposed inside the inflatable balloon, and an impeller disposed inside the heating assembly. The balloon catheter may include a handle assembly secured to the proximal end of the cannula. The handle assembly may include a fluid fill port for introducing fluid into the inflatable balloon and at least one element (e.g. a fluid fill valve) for controlling operation of the balloon catheter. In one embodiment, fluid may be introduced into the inflatable balloon automatically using a system controller coupled with the balloon catheter.

In one embodiment, the heating assembly includes an elongated tube having an outer wall, at least one fluid inlet extending through the outer wall, and a fluid outlet located at a distal end of the elongated tube. The elongated tube may be an elongated heating tube having a heating film overlying the outer wall of the elongated tube for generating heat. A heating film may also cover an inner surface area of the heating tube. In one embodiment, the total area of the at least one fluid inlet is at least equal to the total area of the fluid outlet. In one embodiment, the at least one fluid inlet includes a plurality of fluid inlets. The one or more fluid inlets are preferably located at the proximal end of the heating tube so that the fluid passing through the inlet(s) is positively directed to engage the heating tube as it moves along the length of the heating tube.

The impeller is preferably rotatable for drawing fluid through the at least one fluid inlet and into the heating assembly for heating the fluid. As the fluid passes by the heating assembly, the heating assembly preferably transfers heat to the fluid via convection. The rotatable impeller is adapted to discharge the fluid through the fluid outlet located at the distal end of the elongated tube so as to circulate the fluid throughout the inflatable balloon.

In one embodiment, the cannula includes a lumen extending between the proximal and distal ends thereof for introducing a fluid into the inflatable balloon. A pressure monitor may be in communication with the lumen and/or the fluid for monitoring fluid pressure inside the inflatable balloon. The cannula may also include an impeller drive shaft extending therethrough that is coupled with the impeller for rotating the impeller. The drive shaft preferably has a distal end that extends beyond a distal end of the impeller and a protective cap may cover the distal end of the drive shaft for spacing the distal end of the drive shaft and the impeller from the inflatable balloon. The spacing provided by the cap may prevent the balloon from becoming damaged by contacting the rotating drive shaft or the rotating impeller. In one embodiment, the protective cap is insertable into an opening at the distal end of the elongated tube. The protective cap may be insertable into the fluid outlet located at the distal end of the elongated heating tube. The protective cap preferably has one or more openings extending therethrough for enabling fluid to pass by the cap when the cap is secured in place.

In one embodiment, the cannula may also have one or more conductive leads extending therethrough. The conductive leads preferably interconnect one or more of the elements at the distal end of the balloon catheter with the system controller. In one embodiment, the conductive leads may provide power for one or more components of the heating assembly disposed at the distal end of the balloon catheter.

The system may also include a controller for controlling operation of the system. The system controller is preferably used for controlling an endometrial ablation procedure. In one preferred embodiment, the system controller includes a microprocessor for running endometrial ablation routines with a pressure monitoring subroutine for monitoring and controlling the pressure level of the fluid within the balloon, a temperature monitoring subroutine for monitoring and controlling the temperature of the fluid within the balloon, and a timer subroutine for monitoring and controlling how long the endometrial layer of the uterus is exposed to the heated fluid. In a highly preferred embodiment, the system controller automatically performs one or more of the steps of an endometrial ablation procedure.

In one embodiment of the present invention, a system for treating uterine disorders includes a balloon catheter with a cannula having a proximal end, a distal end, and a lumen extending between the proximal and distal ends of the cannula. The system preferably includes an inflatable balloon secured to the distal end of the cannula, and an elongated heating tube coupled with the distal end of the cannula and that is disposed within the inflatable balloon. The elongated heating tube desirably has at least one fluid inlet extending though an outer wall of the elongated heating tube and a fluid outlet located at the distal end of the elongated heating tube. The elongated tube may have a heating film covering the outer surface of the tube for generating and transferring heat to fluid flowing near the elongated heating tube.

The system also preferably includes an impeller disposed inside the elongated heating tube. The impeller is rotatable for drawing fluid through the at least one fluid inlet and into the elongated heating tube for transferring heat from the elongated heating tube to the fluid, and for discharging the heated fluid from the fluid outlet for circulating the heated fluid throughout the inflatable balloon. A protective cap may cover the fluid outlet at the distal end of the elongated heating tube for preventing the impeller from contacting the inflatable balloon. The system may include a controller connected with the balloon catheter for monitoring and controlling the temperature of the elongated heating tube, controlling rotation of the impeller, and monitoring and controlling fluid pressure within the inflatable balloon.

In one embodiment of the present invention, a system for treating uterine disorders includes a balloon catheter with a cannula having a proximal end and a distal end, an inflatable balloon secured to the distal end of the cannula, and a heating assembly coupled with the cannula and being disposed within the inflatable balloon, the heating assembly having a fluid inlet and a fluid outlet. The system may include an impeller disposed inside the heating assembly. The impeller is preferably rotatable for drawing fluid through the fluid inlet and into the heating assembly, and for discharging the fluid from the heating assembly through the fluid outlet for circulating the fluid within the inflatable balloon. The system also preferably includes a system controller for controlling the pressure level and the temperature of the fluid inside the balloon, and controlling the length time of an endometrial ablation procedure.

In one embodiment, once a balloon catheter is positioned within a uterine cavity, fluid is introduced into the inflatable balloon. The fluid is heated, preferably by a heating tube, and circulated within the uterine cavity to heat the lining of the cavity to sufficiently damage the endometrial lining. The heater tube desirably has one or more films coated over the outer diameter of the tube that are adapted to generate heat. An impeller is located along the inner diameter of the heater tube to circulate the fluid. The arrangement of the impeller relative to the heater tube positively ensures that the circulated fluid will pass by the inner diameter surface of the heater tube, which allows the fluid to more effectively absorb heat for reducing the heater temperature set point to heat the fluid to a certain temperature in comparison to the arrangement of having an agitator at the distal end of the heater. Moreover, as a result of fluid being positively moved through the heater, the fluid within the balloon is more efficiently heated and circulated, thereby resulting in a more consistent balloon surface temperature.

In one embodiment of the present invention, a balloon catheter has an impeller located along the inner diameter of a heating assembly, such as a heating assembly having an elongated heating tube. Although the present invention is not limited by any particular theory of operation, it is believed that the arrangement of the impeller relative to the heating assembly improves overall fluid circulation inside the balloon, which improves thermal transfer from the heater to the fluid, and which results in uniform temperature distribution around the outer surface of the balloon. The more uniform temperatures around the outer surface of the balloon promote more uniform treatment of the uterine tissue. In addition, the improved heat transfer between the heating assembly and the fluid results in a reduction in the amount of energy required to heat the fluid. Moreover, better heat transfer enables the system to have a reduced temperature set point while still achieving an appropriate temperature at the outer surface of the balloon.

In one embodiment, the heating assembly includes a tube, such as a metal tube, having an outer diameter and a heating film coated over the outer diameter of the tube. The heating tube has one or more fluid inlets located adjacent the proximal end of the tube and a fluid outlet located at the distal end of the tube. Heat is transferred from the tube to the fluid as fluid passes inside the tube between the proximal end distal ends of the tube. The system includes the rotatable impeller disposed inside the tube for circulating the fluid through the tube and throughout the balloon. The arrangement of the impeller to the heater tube positively ensures that the circulated fluid will pass by the inner diameter surface of the heater tube, which allows the fluid to better absorb heat, thereby reducing the heater temperature set point to heat the fluid to a certain temperature in comparison to the arrangement of having an agitator at the distal end of the heater. In addition, because fluid is positively moved through the heater, fluid within the balloon is mixed, leading to a more consistent balloon surface temperature.

These and other preferred embodiments of the present invention will be described in more detail below.

BRIEF DESCRIPTION OF THE DRAWING

FIG. 6A shows another side view of the distal end of the balloon catheter shown in FIG. 5A.

FIG. 6B shows a cross-sectional view of the distal end of the balloon catheter shown in FIG. 6A.

FIG. 7A shows a side elevational view of a heater assembly at the distal end of the balloon catheter shown in FIG. 6A.

FIG. 7B shows a cross-sectional view of the heater assembly shown in FIG. 7A.

DETAILED DESCRIPTION

Figure 1:
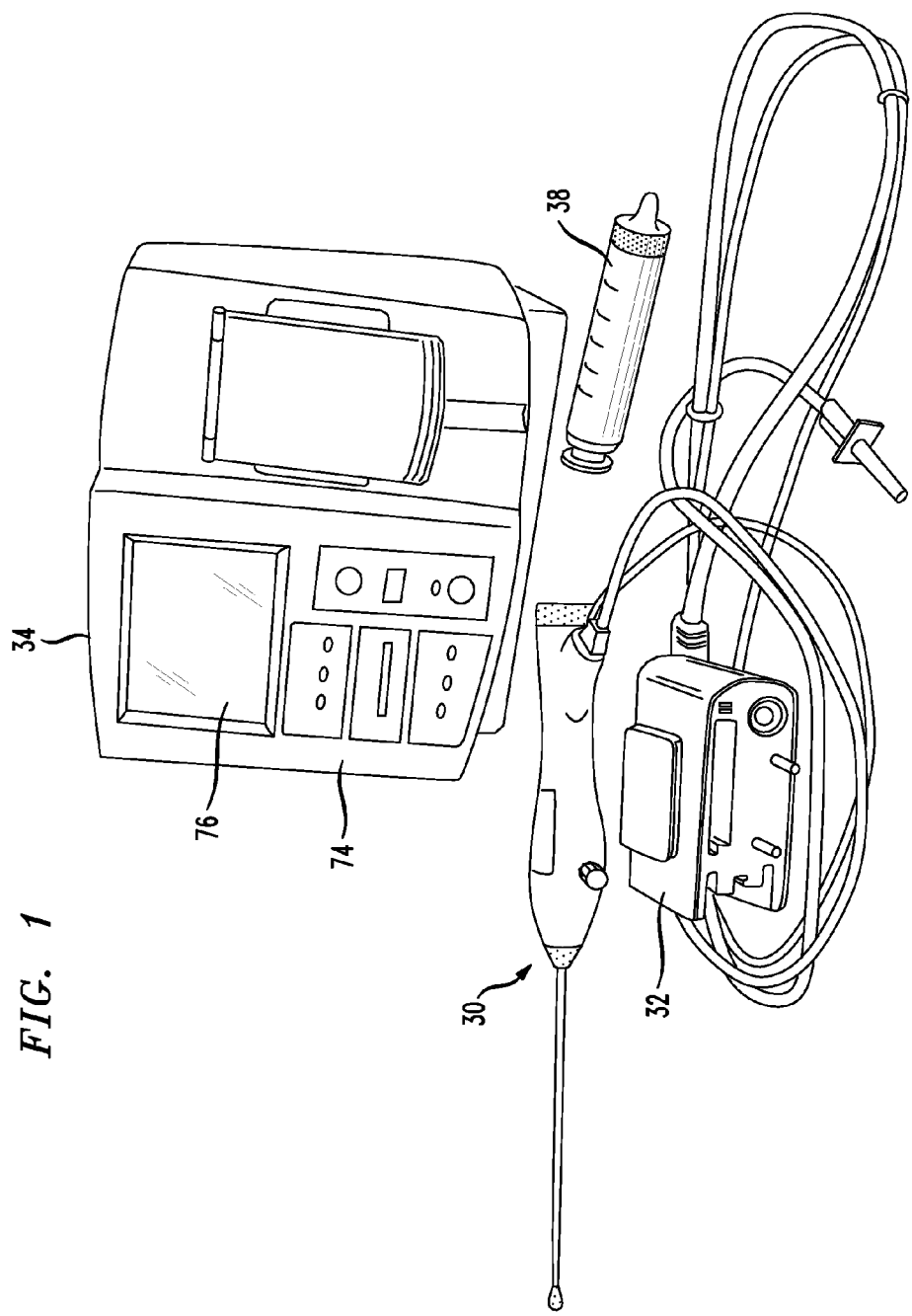
FIG. 1 shows a system used for endometrial ablation procedures including a system controller, a balloon catheter, a cartridge for connecting the balloon catheter to the system controller, and a syringe, in accordance with one embodiment of the present invention.

The headings used herein are for organizational purposes only and are not meant to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

In one embodiment, the present invention discloses a system including a balloon catheter having a heating assembly disposed inside an inflatable balloon and a rotatable impeller located inside the heating assembly. The impeller is rotated by a drive shaft for drawing fluid into contact with the heating assembly, passing the fluid from one end of the heating assembly to the other end of the heating assembly, discharging the fluid from a distal end of the heating assembly, and circulating the fluid inside the inflatable balloon. The balloon catheter system is used to treat uterine disorders in women, such as menorrhagia, by inserting the balloon catheter into the patient's uterus and inflating the balloon with the fluid, such as a saline or an aqueous sugar solution. After the balloon is inflated with the fluid, the fluid is heated to a predetermined temperature (e.g. 81° C.) for a period of time that coagulates, ablates, necroses, or destroys the endometrium. Utilization of the balloon catheter system of the present invention effectively curtails the excessive uterine bleeding associated with menorrhagia without requiring surgical removal of the uterus. Although a specific temperature is set forth above, other temperatures may be used and still fall within the scope of the present invention.

A successful endometrial ablation procedure requires controlling the temperature of the fluid within the balloon and the temperature of the outer surface of the balloon. Temperature fluctuations and gradients along the surface of the balloon, which are caused by convection currents of the fluid within the balloon and formation of a static, insulating boundary layer of fluid along the inner surface of the balloon, adversely affects physician control over endometrial necrosis. Thus, systems and methods of the present invention provide mechanical circulation of the fluid within the balloon, which improves the temperature consistency along the surface of the balloon and the efficacy of the endometrial ablation procedure.

Referring to FIG. 1, in one embodiment of the present invention, a system for endometrial ablation procedures includes a balloon catheter 30 insertable into a uterine cavity, a cartridge 32 for connecting the balloon catheter with a system controller 34, and a syringe 38 adapted to hold a fluid that may be introduced into an inflatable balloon and heated inside the balloon during the endometrial ablation procedure. In one embodiment, the syringe is used in manual mode or for emergency evacuation. In one embodiment, fluid is introduced into the balloon using various techniques well-known to those skilled in the art. In one embodiment, the fluid may be introduced into the balloon automatically by the system controller via one or more conduits coupled with the balloon catheter.

Figure 2:
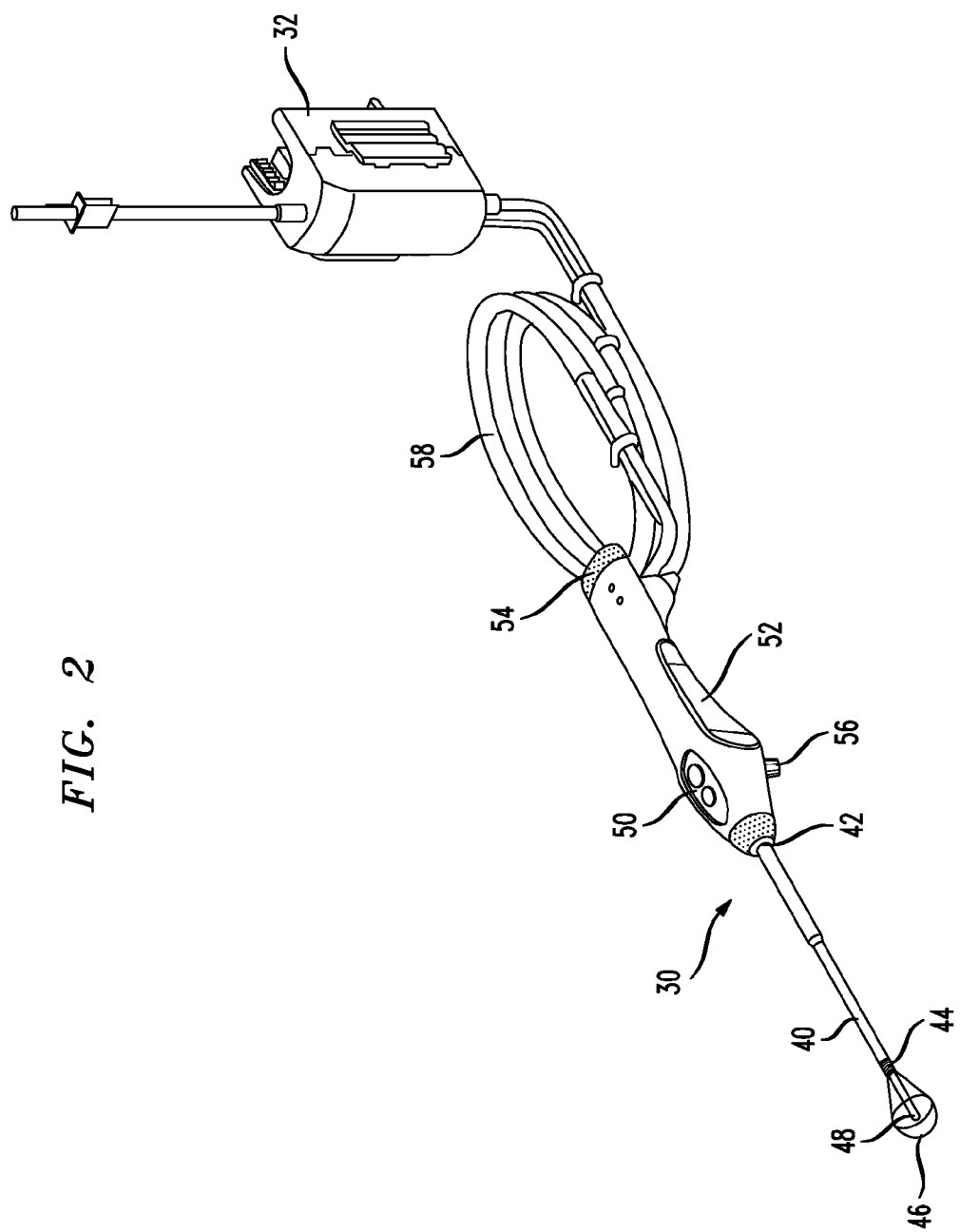
FIG. 2 shows a perspective view of the balloon catheter and the cartridge shown in FIG. 1.
Figure 3:
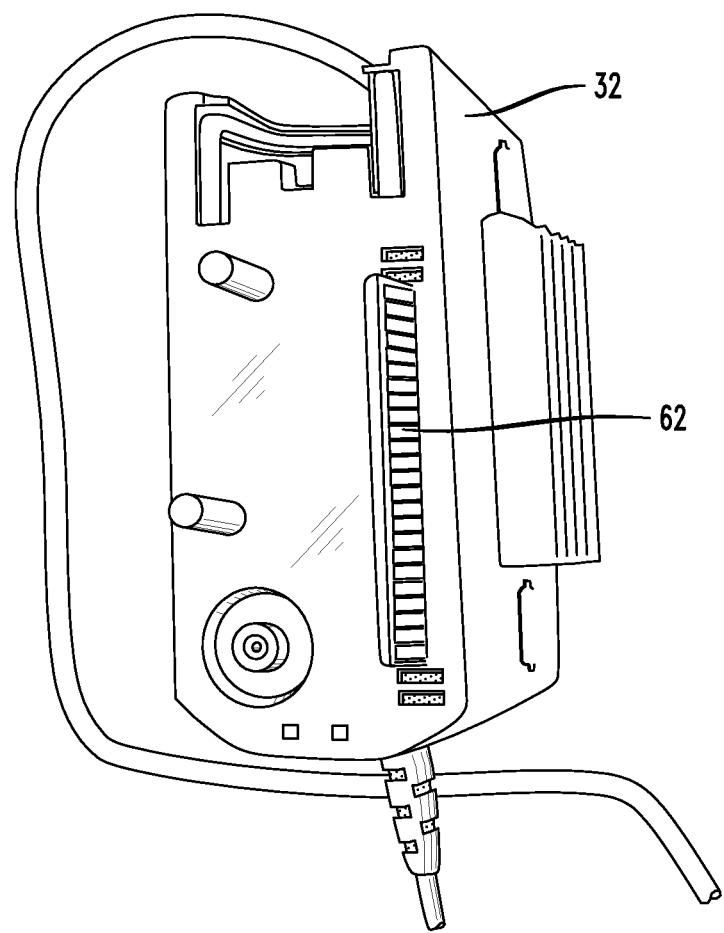
FIG. 3 shows a front view of the cartridge shown in FIGS. 1 and 2.

FIGS. 2 and 3 show the balloon catheter 30 and the cartridge 32 that is used to connect the balloon catheter to the system controller. The balloon catheter 30 includes a cannula 40 having a proximal end 42 and a distal end 44. The distal end of the cannula 40 includes an inflatable balloon 46 that is adapted to receive a fluid, such as a D5W solution or a saline solution. The balloon catheter 30 also includes a heating assembly 48 coupled with the distal end 44 of the cannula 40. The heating assembly 48 is preferably disposed inside the inflatable balloon 46. The system also desirably includes a rotatable impeller (not shown) provided inside the heating assembly for drawing fluid into contact with the heating assembly, positively directing the fluid to pass through the heating assembly, discharging the heated fluid from an outlet at a distal end of the heating assembly, and effectively circulating the fluid throughout the balloon.

Referring to FIG. 2, the balloon catheter 30 also includes a handle 50 that is connected to the proximal end 42 of the cannula. The handle 50 includes a body 52 that is ergonomically designed for a human hand, a fluid fill port 54 for introducing a fluid into the inflatable balloon 46, and a fluid fill valve 56 that is used to control the amount of fluid introduced into the balloon. In addition, the system includes the cartridge 32 and a cable 58 that connects the cartridge with the balloon catheter handle 50. In one embodiment, the fluid may be introduced into the balloon 46 using the cartridge 32 and/or the cable 58.

FIG. 3 shows the front face of the cartridge 32 that is used to couple the balloon catheter with the system controller shown in FIG. 1. The cartridge 32 desirably has an electrical connector 62 that connects with the system controller for providing electrical power to the balloon catheter and/or control over the operation of the balloon catheter. The coupling of the cartridge 32 with the system controller enables a wide variety of critical functions to be performed by the system controller. In one embodiment, the system controller includes a pressure monitor that is in communication with the fluid within the balloon for monitoring the pressure of the fluid inside the balloon. The system controller may also monitor the volume of fluid inside the balloon. In one embodiment, the system controller includes a peristaltic pump that may be used for automatically priming and controlling the pressure level within the inflatable balloon. The system controller may also monitor and/or control an impeller drive shaft for selectively rotating a rotatable impeller provided inside a heating assembly. The system controller may also provide power and/or control signals to the heating assembly, the impeller, and/or other components of the system.

Figure 4:
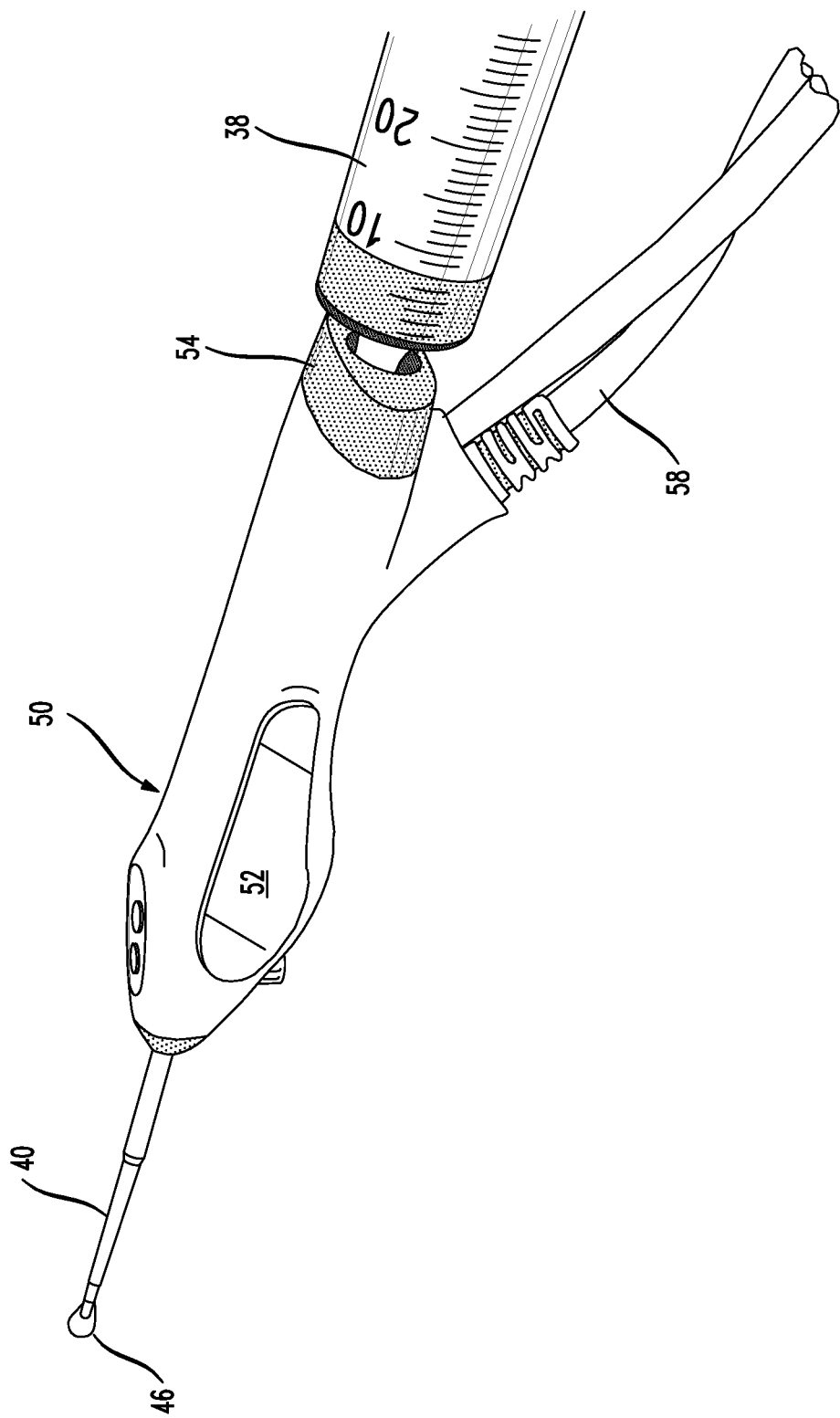
FIG. 4 shows the syringe and the balloon catheter of FIG. 1 coupled together.

Referring to FIG. 4, in one embodiment, the handle 50 of the balloon catheter desirably includes the body 52 having a fluid fill port 54 adapted to receive the syringe 38, and a fluid fill valve 56 for controlling introduction of the fluid into the balloon 46. The handle body 52 is configured to retain the fluid fill port 54, to secure the fluid fill valve 56, and to couple with the cable 58 connecting the balloon catheter with the cartridge. The handle body 52 is preferably shaped to conform to a human hand. In one embodiment, fluid is introduced into the balloon through one or more conduits extending between the handle and the system controller.

The fluid fill valve 56 is used to control the volume of fluid supplied to the inflatable balloon 46. In one embodiment, a pressure conduit is adapted to be interconnected with the system controller to provide monitoring and control of the fluid pressure inside the inflatable balloon. In other embodiments, a pressure transducer may be disposed within the balloon catheter handle 50. The pressure transducer may be electrically connected to the system controller via electrical leads extending through the cable 58. In one embodiment, the system operates in an automatic mode whereby the system controller monitors and/or maintains the fluid pressure inside the balloon.

Figure 5A:
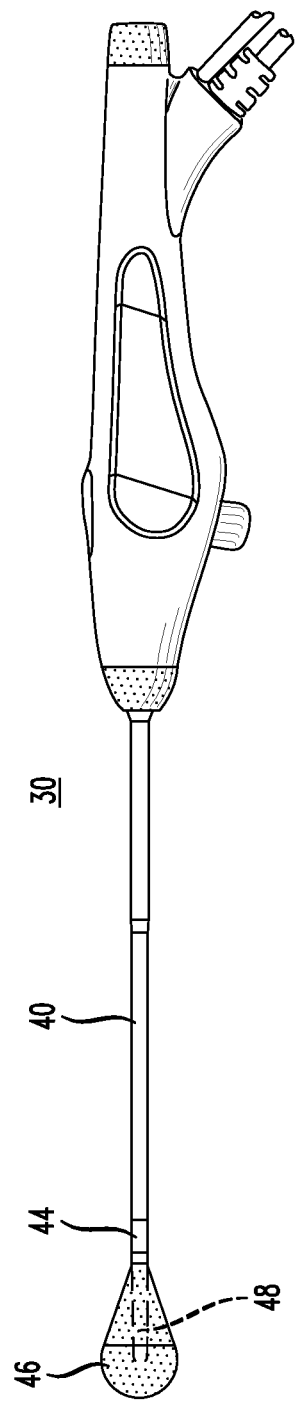
FIG. 5A shows a side elevational view of the balloon catheter shown in FIG. 1.
Figure 5B:
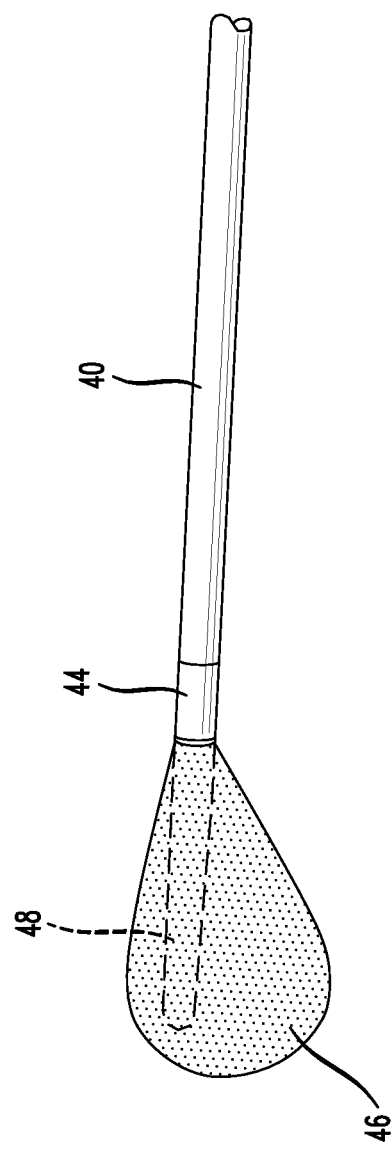
FIG. 5B shows a side view of a distal end of the balloon catheter shown in FIG. 5A.

Referring to FIGS. 5A and 5B, in one embodiment of the present invention, a distal end of the balloon catheter 30 includes the distal end 44 of the cannula 40 and the inflatable balloon 46 connected to the cannula. The balloon catheter also includes the heating assembly 48 extending from the distal end 44 of the cannula. The heating assembly 48 is disposed inside the balloon for heating the fluid introduced into the balloon. The balloon catheter also includes a rotatable impeller (not shown) disposed inside the heating assembly for drawing fluid into engagement with the heating assembly, heating the fluid, and circulating the fluid throughout the inside of the balloon to provide for uniform heating of the outer surface of the balloon.

In certain preferred embodiments of the present invention, the inflatable balloon is made of latex, silicone, or other elastomeric materials. In one embodiment, the inflatable balloon is approximately 3-5 centimeters in length when inflated by fluid. The inflatable balloon is desirably capable of filling the uterine cavity and exerting pressure against the endometrium. The inflatable balloon is desirably capable of withstanding high temperatures without rupturing, and preferably has good heat transfer characteristics to provide efficient heat transfer from the heating assembly to the uterine tissue. The inflation medium or heating fluid is preferably a sterile non-toxic fluid. In one embodiment, the fluid is a solution of five percent (5%) dextrose in water.

Referring to FIG. 1, in one embodiment, the system controller 34 preferably controls operation of the balloon catheter during an endometrial ablation procedure. As such, the system controller preferably has one or more endometrial ablation procedures or subroutines programmed therein. The front face 74 of the system controller desirably includes one or more first visual displays 76 for monitoring the pressure of the fluid inside the inflatable balloon, the temperature level of the fluid inside the inflatable balloon, and the time remaining in a procedure. The visual display 76 may also provide instructions to an operator and/or enable an operator to track the status of an endometrial ablation procedure.

The system controller is adapted to regulate and control the heat applied to the fluid in the inflatable balloon by modulating the electrical voltage or current to the heater assembly or other power source for the heating assembly. The system controller may include a temperature controller which uses temperature sensors such as thermocouples or thermistors for feedback control. The temperature may be controlled to a predetermined level or to a level selected by an operator. The system controller further controls the operating time for which heat is applied to the fluid in the inflatable balloon and monitors the pressure of the fluid in the inflatable balloon. The system controller also initiates and terminates the operation of the rotary drive mechanism which initiates and terminates the rotation of the impeller drive shaft and the impeller. The system controller may incorporate one or more of the features disclosed in commonly assigned U.S. Pat. Nos. 4,949,718 and 5,800,493, the disclosures of which are hereby incorporated by reference herein in their entirety.

Referring to FIG. 6A, in one embodiment of the present invention, the cannula 40 is preferably an elongated tube that may be flexible and/or semi-rigid. In one embodiment, the cannula is made of silicone with a metal tube provided at the center. In other embodiments, the cannula may be made of materials such as acrylonitrile-butadiene-styrene (ABS), polyvinyl-chloride (PVC), or polyurethane. The cannula is preferably insertable into the uterus, while providing support necessary for manipulating the position of the inflatable balloon within the uterus. The cannula 40 desirably has a sufficient length from the inflatable balloon to the balloon catheter handle to extend through a patient's vaginal canal, the cervix and into the uterus. Placement of the apparatus may be aided by virtue of scale gradations provided on the outer surface of the cannula to indicate the depth of insertion of the inflatable balloon into the uterine cavity.

In one embodiment of the present invention, the cannula 40 desirably has a lumen adapted to receive a fluid, an impeller drive shaft for rotating the impeller, and electrical leads for the heater assembly, thermistors, the impeller and/or any other components required to be interconnected with the system controller. The lumen preferably extends along the length of the cannula 40 between the balloon catheter handle and the distal end of the cannula. The lumen may be arranged in any configuration required while maintaining the structural integrity of the cannula shaft. The cross-sectional shape of the lumens may be annular, hemispherical, or any other shape suitably required for performance of the device.

Referring to FIG. 6B, in one embodiment, an impeller drive shaft 66 is positioned centrally within the lumen 92 so that contact along the length of the drive shaft with the wall of the lumen is minimized for reducing friction. The proximal end of the drive shaft 66 is desirably in communication with the system controller. The distal end of the lumen 92 is in communication with the inside of the heating assembly. Electrical leads interconnecting the system controller with the heating assembly, the impeller and/or thermocouples may also extend through the lumen 92. In one embodiment, the space between the inner diameter of the heating tube and the drive shaft for the impeller is used exclusively for introducing fluid into and removing fluid from the inflatable balloon. In one embodiment, the electrical leads for the heater and the thermistor are located outside the heating tube and may be embedded in silicone.

Referring to FIGS. 7A and 7B, in one embodiment of the present invention, the distal end of the balloon catheter 30 includes a heating assembly 48 projecting from a distal end 44 of the cannula 40. In FIGS. 7A and 7B, the inflatable balloon at the distal end of the balloon catheter has been removed so that the heating assembly and the impeller may be clearly seen. The heating assembly 48 has a proximal end 100 coupled with the distal end 44 of the cannula 40 and a distal end 102 remote therefrom. The heating assembly 48 preferably includes an elongated tubular member extending between the proximal end 100 and the distal end 102. A heating film may overlie the outer surface of the elongated tubular member for generating heat. The elongated heating tube may incorporate one or more of the medical heater technologies sold under the trademark MICROPEN by MicroPen Technologies of Honeoye Falls, N.Y. In one embodiment, the heating element may be made of any thermally conductive material. In one embodiment, the heating element is preferably a metal tube such as a stainless steel metal tube. A conductive film may be provided over the outer surface of the metal tube. The conductive film is preferably adapted to generate heat that is transferred to fluid passing through the heating assembly. The conductive film may be a conductive ink that is printed over the outer surface of the tube. The conductive ink may be printed in a pattern. The conductive film may also be provided over an inner surface of the heating tube.

In one embodiment, the heating assembly may incorporate one or more of the fluid heating elements sold by Watlow Electric Manufacturing Company of St. Louis, Mo., including the heater technology disclosed in U.S. Pat. No. 6,944,394, the disclosure of which is hereby incorporated by reference herein. The balloon catheter 30 desirably includes a rotatable impeller 104 that is disposed within the tubular heating assembly 48. In one embodiment, the impeller has a length that lies completely within the extent of the heating assembly. As such, the heating assembly may entirely encompass the impeller.

In one highly preferred embodiment, the distal end 102 of the heating assembly is distal to the distal end 105 of the impeller 104. The impeller 104 is connected to an impeller drive rod 66 that rotates the impeller 104 inside the heating assembly 48. The impeller drive rod 66 is preferably about 0.5 to 1.0 millimeters in diameter, and desirably has some flexibility. The impeller drive rod may be made of stainless steel or spring steel. The impeller drive rod desirably extends the entire length of the balloon catheter from the distal end of the balloon to the balloon catheter handle. In other embodiments, a co-axially wound cable is also suitable. A distal end 106 of the impeller drive rod 66 is covered by a protective cap 108 that is adapted to prevent the inflatable balloon from being damaged by the distal end 106 of the drive rod or the distal end of the heating assembly 48.

Figure 8:
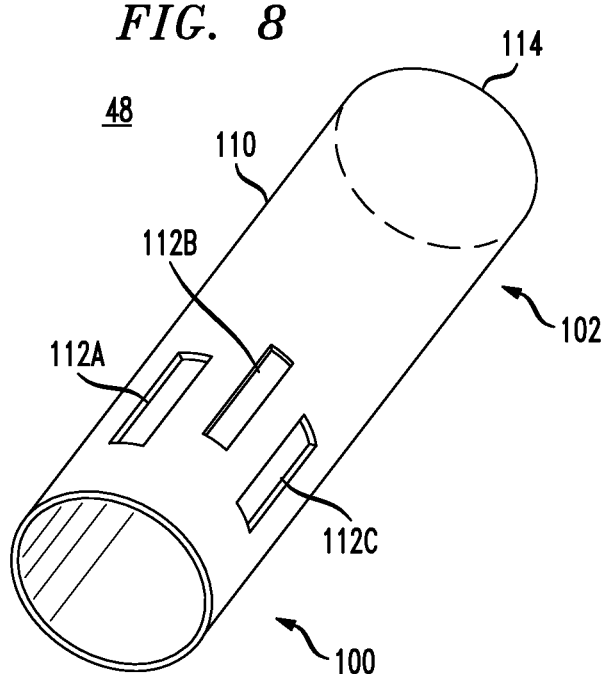
FIG. 8 shows a perspective view of the heater assembly shown in FIGS. 7A and 7B.

FIG. 8 shows a perspective view of a section of the heating assembly 48, in accordance with one embodiment of the present invention. The heating assembly 48 includes an elongated tubular member having a proximal end 100 and a distal end 102. The heating assembly 48 includes an outer wall 110 having an outer surface. One or more films adapted to generate heat may overlie the outer surface of the outer wall. The heating assembly 48 includes a series of fluid inlets 112A, 112B, 112C that enable fluid to pass from outside the heating assembly to inside the heating assembly. As the fluid passes through the fluid inlets, the fluid preferably contacts the heating assembly for heating the fluid. The heating assembly 48 also includes a fluid outlet 114 provided at a distal end 102 thereof for discharging the heated fluid from the distal end of the heating assembly, and for efficiently circulating the fluid throughout the balloon. The total area of the fluid inlets 112A-112C is preferably at least equal to the total area of the fluid outlet 114. The fluid inlets are preferably located at the proximal end 100 of the heater tube 48 so as to increase contact between the fluid and the heater tube as the fluid flows along the length of the heater tube.

The elongated heating tube had an inner diameter that is slightly larger than the outer diameter of the impeller. The action of the rotating impeller causes circulation of the fluid through the heating tube and within the balloon.

Figure 9:
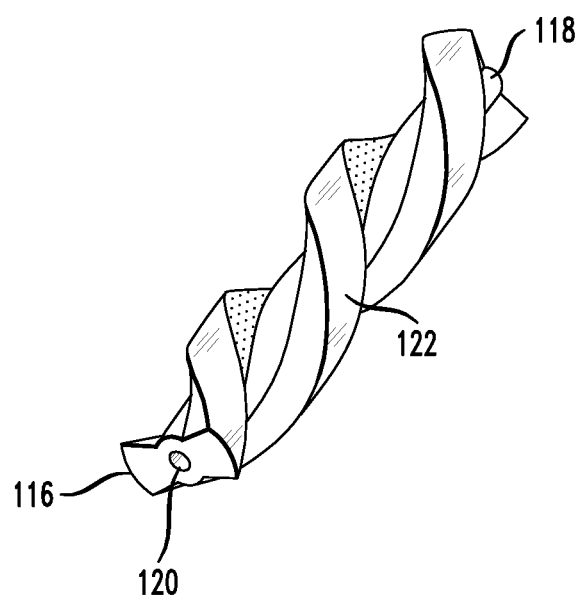
FIG. 9 shows a perspective view of an impeller disposed inside the heater assembly of FIG. 8.

FIG. 9 shows a rotatable impeller 104 in accordance with one embodiment of the present invention. The impeller 104 includes a proximal end 116, a distal end 118 and a drive shaft lumen 120 that extends between the proximal and distal ends. The impeller 104 preferably includes helically wound threads 122. The impeller may have a single thread or multiple threads. In one preferred embodiment, the impeller is a double thread impeller that extends between the proximal and distal ends thereof. In other preferred embodiments, the impeller may include blades or fins for circulating fluid. As the impeller 104 is rotated by the drive rod 66 (FIG. 7B), the helical screw threads 122 circulate the fluid inside the balloon. Referring to FIGS. 8 and 9, in one embodiment, as the impeller 104 rotates, fluid is drawn into the heater 48 through the fluid inlets 112A-112C, and discharged from the heater through the fluid outlet 114. The impeller may be made of polymer materials such as polycarbonate (PC), latex strips, polyethylene (PE), polyethylenetherapthalate (PET) or other suitable materials such as metals and alloys.

In one embodiment, the heating assembly includes a fluid thermister for monitoring the temperature of the fluid inside the balloon. The heating assembly 48 also preferably includes a heater thermistor for monitoring the temperature of the heater.

Referring to FIGS. 7A and 7B, the heater assembly 48 includes an elongated tube having a proximal end 100, a distal end 102, and a tubular outer wall 110 extending therebetween. The balloon catheter include the rotatable impeller 104 disposed within the heater assembly. The rotatable impeller 104 is rotated by the impeller drive shaft 66 that extends through the cannula 40 and the heater assembly 48. The distal end 106 of the drive shaft 66 is preferably covered by the protective cap 108. In one embodiment, the protective cap 108 includes a central hub 130 having a curved or a convexly curved distal surface 132 and an opening 134 that surrounds the central hub 130. The opening 134 enables the fluid discharged from the discharge opening 114 of the heater to pass therethrough.

In one embodiment, when the impeller rotates, pressure gradients formed by the helical threads 122 on the impeller 104 draw fluid into the heating assembly through the fluid inlet ports. The rotating impeller also causes fluid to exit the distal end of the heating assembly through the fluid outlet and through the protective cap. Thus, a circulation path of fluid within the balloon, proximal to distal to proximal, is developed. The circulation path of the fluid preferably circulates the fluid throughout the entire balloon and preferably minimizes temperature gradients at the outer surface of the inflated balloon.

Figure 10B:
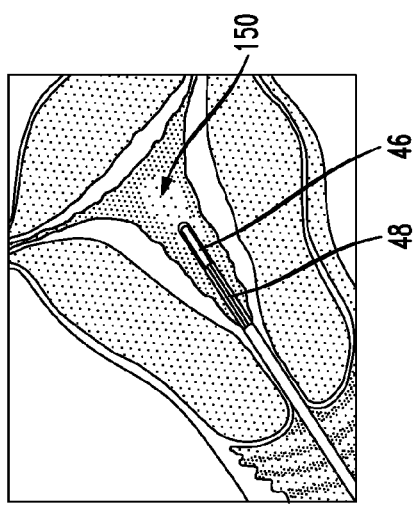
FIGS. 10A-10G show the steps of an endometrial ablation procedure using the system shown in FIG. 1, in accordance with one embodiment of the present invention.
Figure 10D:
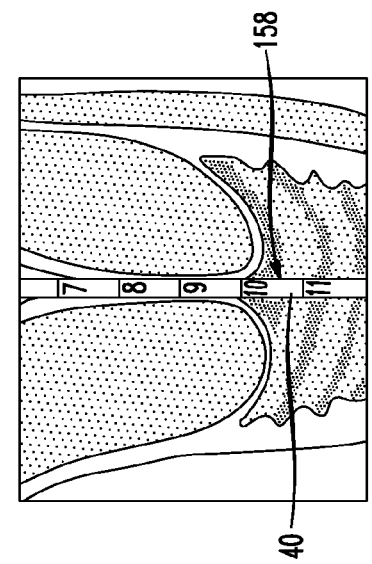
Figure 10A:
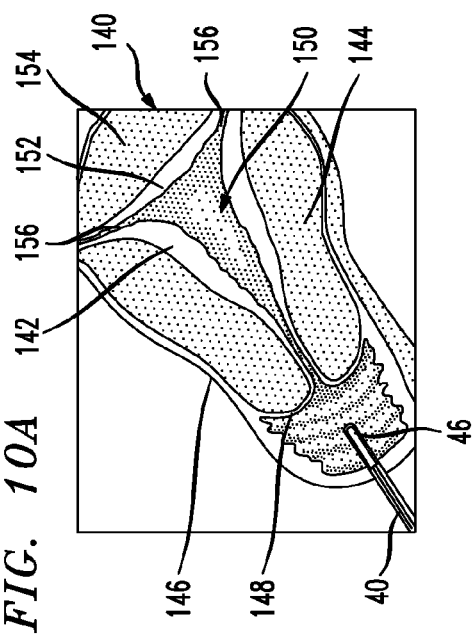

FIGS. 10A-10G show a balloon catheter system during an endometrial ablation procedure, in accordance with one embodiment of the present invention. Referring to FIG. 10A, the distal end of the cannula 40 is aligned for insertion into a uterus 140. The uterus 140 has three basic layers, i.e., the endometrium 142, the myometrium 144 and the outer layer or serosa 146. The balloon catheter is inserted into the uterus through the cervix 148, and is advanced into the uterine cavity 150 until it reaches the distal wall 152 proximate the fundus 154. The inflatable balloon 46 is adapted to conform to the shape of the uterine cavity 150 so as to provide for effective heat transfer from the heating assembly to the endometrium 142. When the balloon is inflated with a fluid, the distal portions of the balloon preferably extend into each cornu 156 of the uterus 140.

Figure 10C:
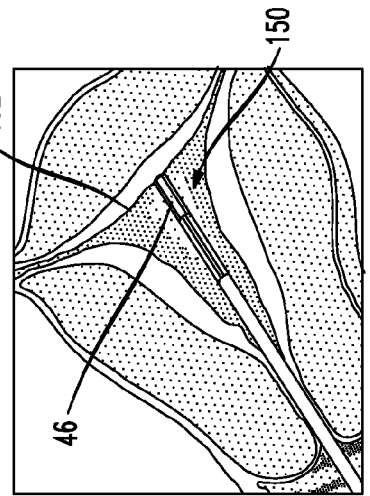

Referring to FIG. 10B, with the balloon 46 deflated, the distal end of the balloon catheter is advanced until the balloon 46 and the heater 48 are disposed inside the uterine cavity 150. Referring to FIG. 10C, the distal end of the balloon catheter is further advanced until the distal end of the balloon 46 contacts the distal wall 152 of the uterine cavity 150. Referring to FIG. 10D, gradations 158 are preferably provided on the outer surface of the cannula 40 to provide a visual indicator of when the balloon catheter has been inserted to a proper depth inside the uterus.

Figure 10E:
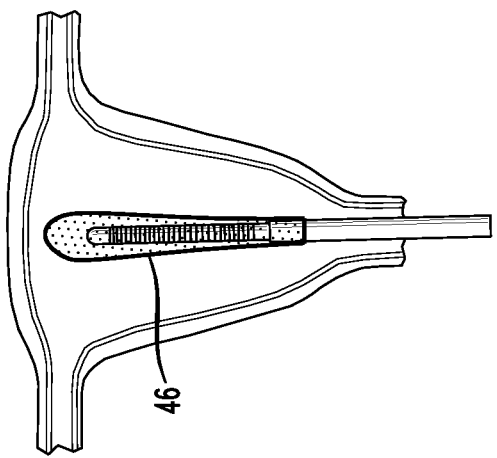
Figure 10F:
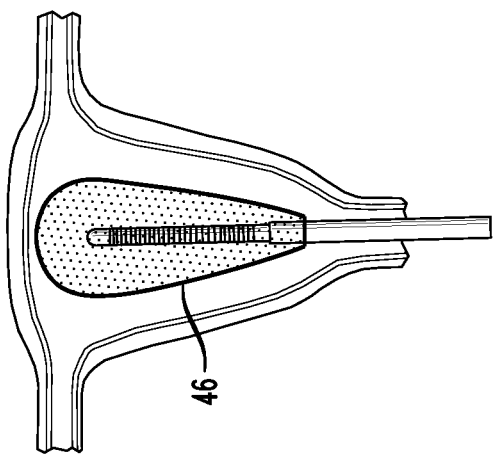
Figure 10G:
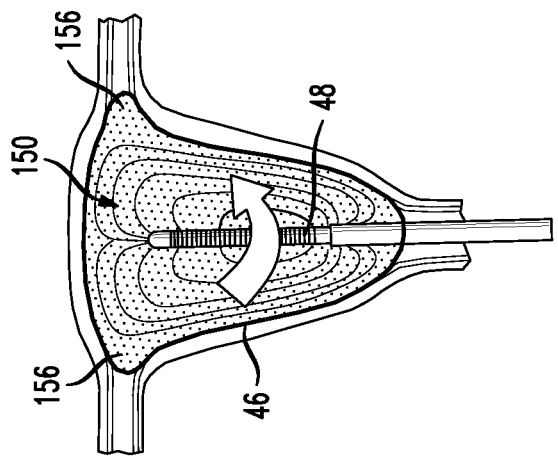

Referring to FIGS. 4 and 10E, a fluid-filled syringe 38 may be coupled with the fluid fill port 54 of the balloon catheter handle 50 so as to introduce the fluid into the inflatable balloon 46. The fluid fill valve 56 may be manipulated for controlling the volume of fluid introduced into the inflatable balloon. In other embodiments, the fluid may be automatically introduced into the balloon via a peristaltic pump, such as a peristaltic pump in communication with a system controller. Referring to FIG. 10F, as the fluid is introduced into the balloon 46, the internal pressure of the fluid in the balloon is continuously monitored to insure that the fluid pressure inside the balloon does not exceed safe pressure levels. Referring to FIG. 10G, a sufficient volume of fluid is preferably introduced into the inflatable balloon 46 until the outer surface of the balloon conforms to the walls of the uterine cavity 150. As the balloon is filled, the pressure level of the fluid is continuously monitored to insure safe pressure levels are maintained within the balloon.

Figure 11:
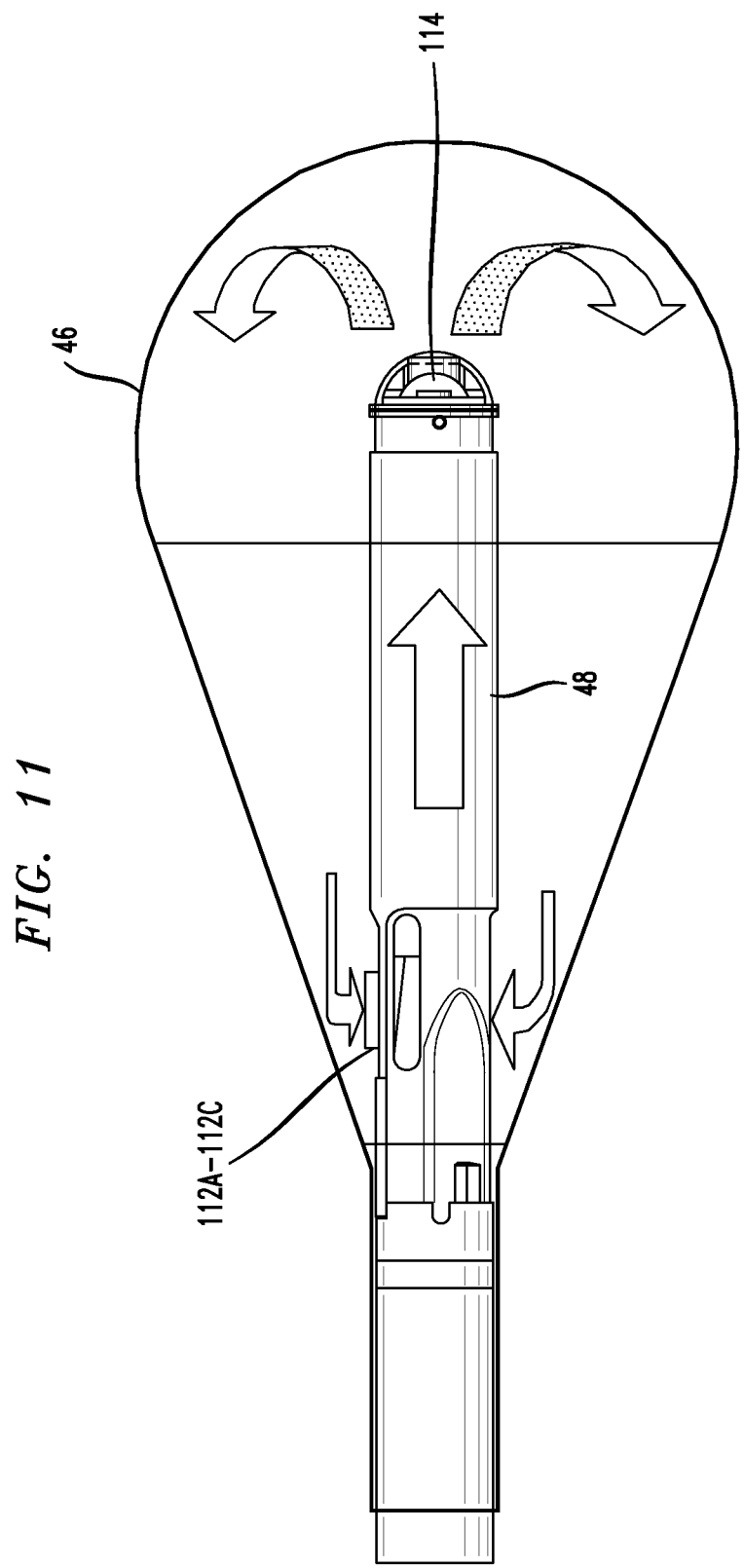
FIG. 11 shows the path of fluid circulating through the distal end of the balloon catheter of FIG. 2 during one stage of an endometrial ablation procedure, in one embodiment of the present invention.

Referring to FIGS. 10G and 11, after a sufficient volume of fluid has been introduced into the balloon 46, the system controller preferably activates the heater 48 for heating the fluid inside the balloon 46. In one embodiment, the heater temperature set point is preferably set to a temperature of about 81° C. to achieve a preferred balloon surface temperature. In other embodiments, the heater temperature set point is set to a temperature that is sufficient for successfully completing endometrial ablation procedures. Thus, various heater temperature set points may be used and still fall within the scope of the present invention. The impeller (not shown) inside the heater assembly 48 is rotated for drawing the fluid into the fluid inlets 112A-112C of the heating assembly and discharging the heated fluid from the fluid outlet 114 at the distal end of the heating assembly 48. FIG. 11 shows the circulation path of the fluid inside the balloon. The fluid is preferably discharged from the fluid outlet 114 at the distal end of the elongated heating tube and circulated throughout the balloon, including the portions of the balloon in the vicinity of the cornua 156 (FIG. 10G). The fluid is drawn into the fluid inlets 112A-112C and directed toward the fluid outlet by the rotating impeller. The fluid is then directed through the inside of the heating tube toward the distal end of the heating tube. Heat is transferred from the heating assembly to the fluid as the fluid passes closely by the inner surface of the heating assembly.

In one embodiment, heat is applied to the fluid by applying electric voltage to the heating assembly, and the impeller is rotated for circulating the fluid throughout the balloon. The rotation of the impeller preferably continues for the duration of the heat therapy. At the end of the procedure, the heating assembly is deactivated. After the power to the heating assembly is turned off, it is preferable to maintain the rotation of the impeller until the fluid is drained from the balloon.

Figure 12:
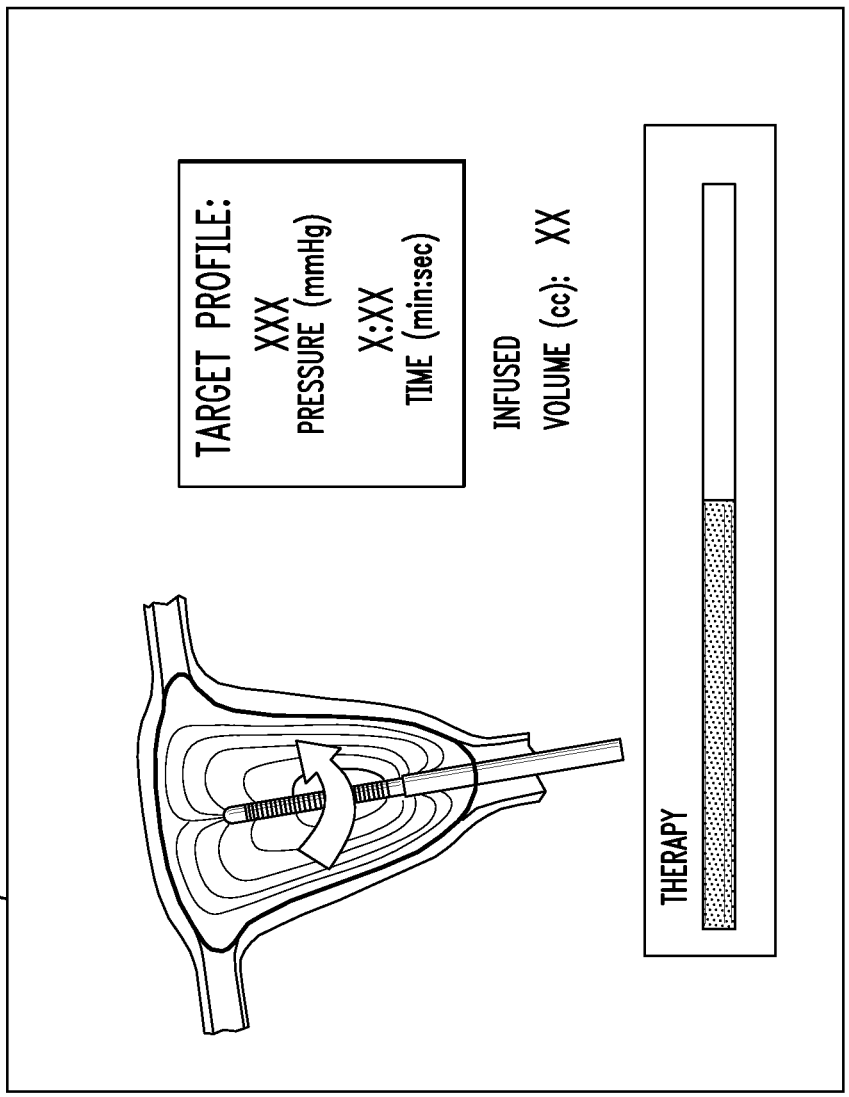
FIG. 12 shows a section of a visual display provided on a front face of the system controller shown in FIG. 1.

Referring to FIG. 12, during the endometrial ablation procedure, an operator may continuously monitor the visual display screen provided on the front face of the system controller 34 to insure that the procedure is advancing within proper parameters. As noted above, an operator will monitor the pressure of the fluid inside the balloon, the temperature of the heated fluid inside the balloon and the amount of time remaining in the procedure. The operator may also monitor the visual display screen to receive instructions and/or observe the status of the procedure. In one embodiment, the pressure and/or temperature may be automatically modulated by the controller.

After the endometrial ablation procedure is completed, the fluid inside the balloon is withdrawn from the balloon through the cannula. The fluid is preferably cooled inside the balloon before it is withdrawn through the cannula. As the fluid is withdrawn, the inflatable balloon collapses. After all of the fluid has been withdrawn from the inflatable balloon, the inflatable balloon returns to its initial collapsed position. The distal end of the balloon catheter may then be removed from the uterine cavity.

Figure 13:
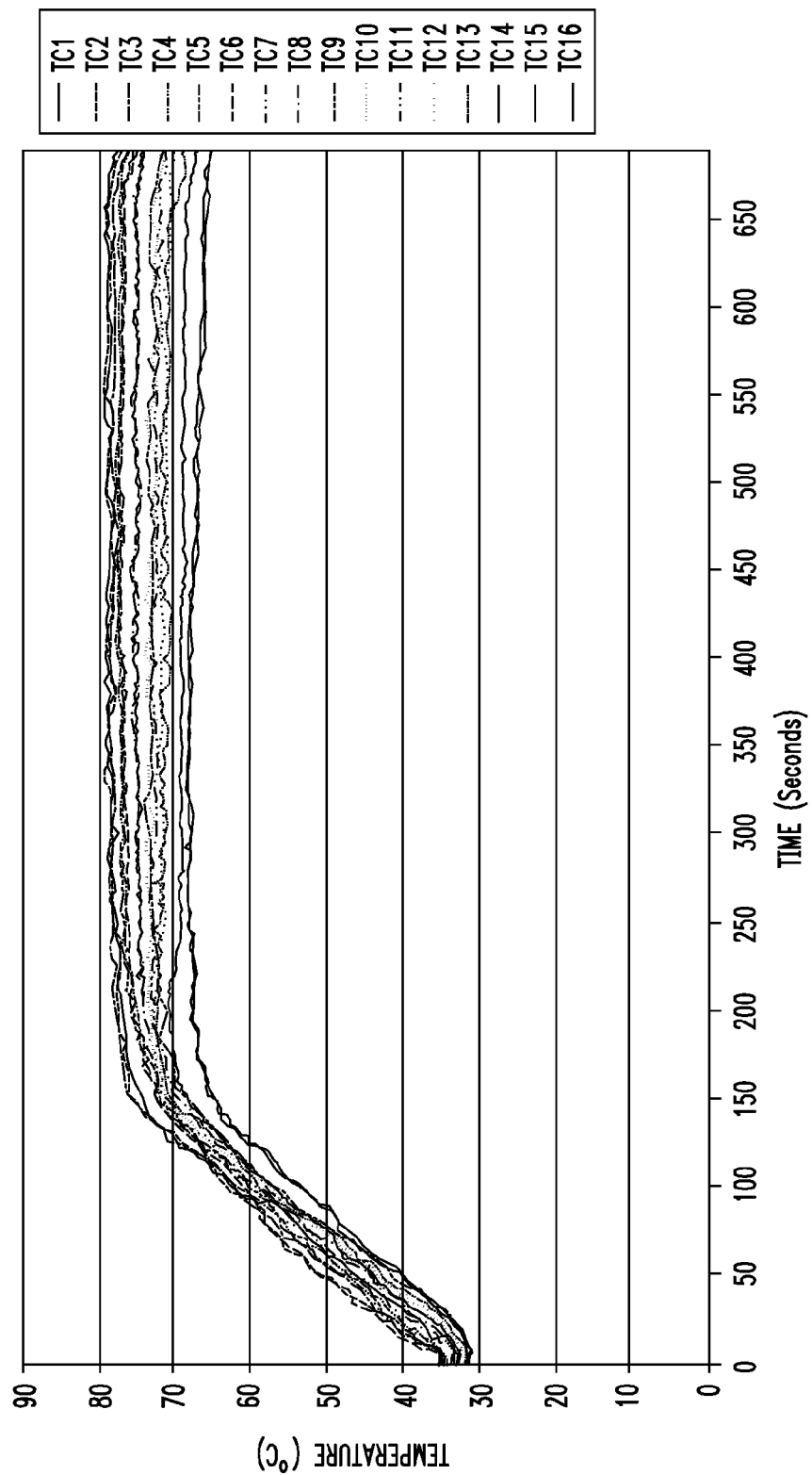
FIG. 13 shows a temperature versus time graph plotting the performance of a prior art endometrial ablation system.
Figure 14:
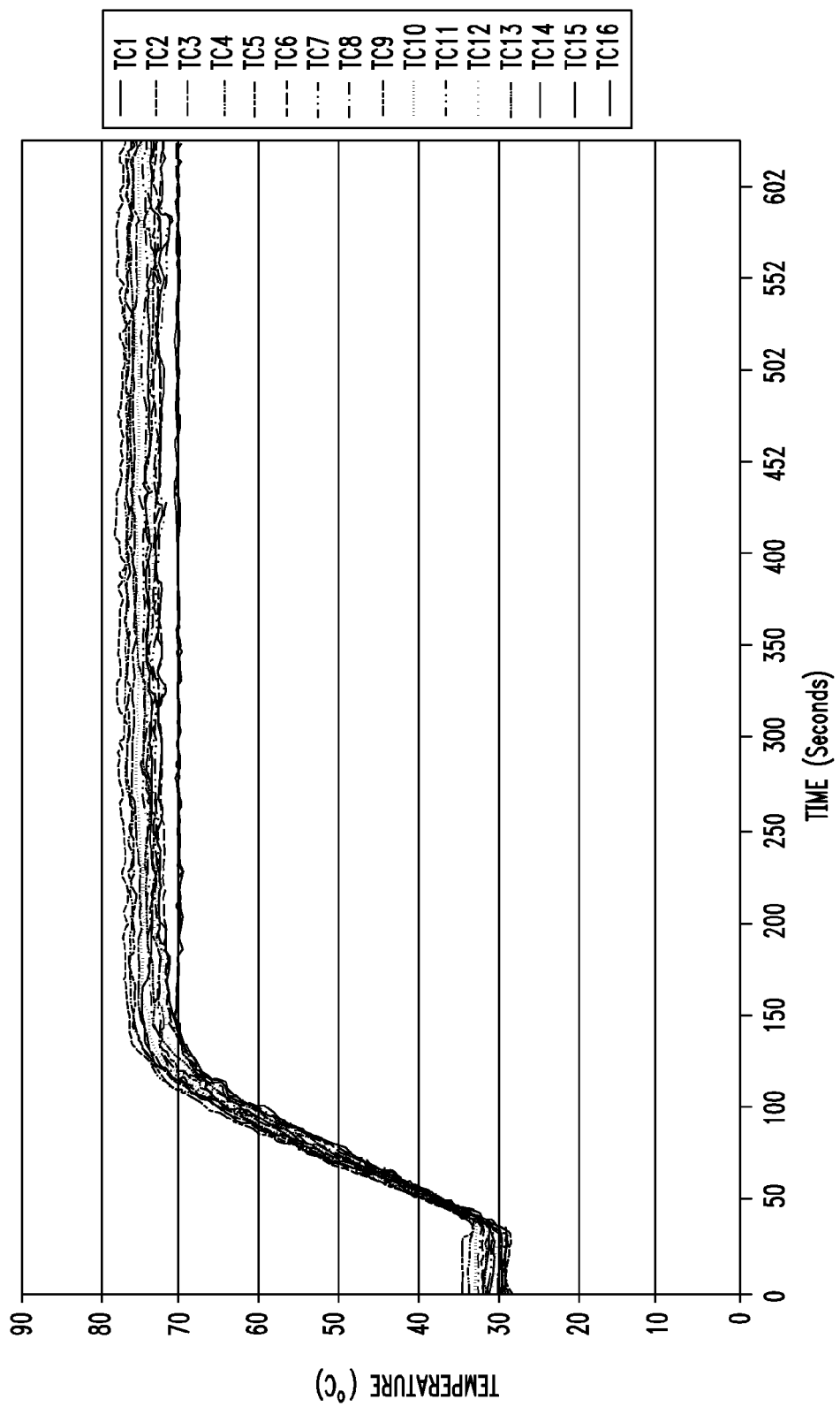
FIG. 14 shows a temperature versus time graph plotting the performance of an endometrial ablation system, in accordance with one embodiment of the present invention.

FIG. 13 is a graph showing the performance of a prior art balloon catheter system having an externally mounted agitator for circulating fluid inside a balloon. As indicated by the graph, the temperature set point is 87° C. and the temperature difference between the highest and lowest curve is relatively broad. In contrast, FIG. 14 shows a graph of temperature versus time when using the balloon catheter system of the present invention. As shown in FIG. 14, the temperature set point is 81° C. and the temperature difference between the highest and lowest curve is smaller than when using the prior art device. Thus, the two graphs show the improved performance that may be obtained when using the balloon catheter system of the present invention, namely better control of the temperature of the fluid, more efficient heating of the balloon, more uniform heating of the fluid in the balloon, and more uniform heating of the outer surface of the balloon.

Set forth below is an endometrial ablation procedure in accordance with one embodiment of the present invention. The disclosed method steps are not meant to limit the scope of the invention. Although exact steps having a particular order are set forth below, other embodiments may place the steps in a different order and still fall within the scope of the present invention. Moreover, other embodiments may use only one of the steps, or a limited number of the steps, disclosed below and still fall within the scope of the present invention. In one embodiment, one or more of the steps may be performed automatically by a system controller.

In one embodiment, the following components are assembled: a sterile disposable silicone balloon catheter, a syringe (e.g. a 30 cc syringe), a cartridge, a cable connecting the catheter and the cartridge, and a system controller. The following medical supplies may be assembled: 50 cc sterile injectable 5% dextrose in water solution (D5W), a tenaculum, a (weighted) speculum, uterine sound for determining the depth of the uterus, cervical dilator(s), and a sterile drape for one or more of the components identified above. In one embodiment, an intravenous (IV) bag containing 100 cc of D5W is utilized. The 100 cc IV bag is highly preferred for embodiments in which one or more of the steps are performed automatically, such as by being performed automatically using a system controller.

A sterile package is opened to unpack the balloon catheter and the syringe. The components may be disinfected. After insuring that the system controller power is off, a power cord may be plugged into the back of the system controller and into a wall outlet.

The cartridge preferably includes one or more connectors to connect the balloon catheter to the system controller. The cable and the cartridge are visually inspected to ensure there are no defects or signs of wear. The cable is draped with the sterile drape, if necessary, and the cartridge is connected to the system controller.

The operator may then turn on the power for the system controller. The message display may read: REVISION N.NN—INITIALIZING, then CONNECT CATHETER. Once the catheter is connected, the message display will read: PRIME CATHETER. A pressure line may be connected with the system controller before the balloon catheter is filled with fluid, or the device may not function properly.

In one embodiment, the balloon is primed automatically by the controller. In one embodiment, an operator may prime the catheter by adding fluid to the balloon. When adding fluid during priming, an operator may ensure that the balloon fully opens so that none of its sides are touching. In one embodiment, a 30 cc syringe is filled with up to 20 cc of sterile injectable 5% dextrose in water (D5W). The syringe is connected with the fluid fill port at the proximal end of the balloon catheter. The connection of the syringe to the fluid fill port should not be over-tightened. After the syringe is connected, the tip of the balloon catheter is pointed downward, and the fluid fill valve on the top of balloon catheter handle is depressed. The plunger of the syringe may be depressed slowly to fill the balloon with up to 20 cc of D5W. When filling, the operator preferably ensures that the pressure of the fluid does not exceed 200 mmHg indicated by the pressure display on the system controller. The fluid fill valve may be depressed to evacuate fluid and air from balloon to a negative pressure of −150 to −200 mmHg (indicated by the pressure display on the controller. In certain embodiments, an operator may need to purge air from the syringe several times to attain the desired negative pressure reading. An operator preferably releases a trumpet valve to maintain negative pressure. Air is preferably completely evacuated to optimize the function of the device. During priming, when catheter pressure is <−150 mmHg, the message display on the system controller will read: PRIME CATHETER<−150 mmHg.

During evacuation, −200 mmHg negative pressure should not be exceeded. Excessive negative pressure may lead to greater pressure fluctuation during therapy. The negative pressure creates a low-profile balloon for insertion into a uterus. Negative pressure is preferably maintained for at least 10 seconds before proceeding. Once catheter pressure is >−150 mmHg, the Message Display may read: INSERT CATHETER & FILL WITH D5W. If negative pressure cannot be maintained for 10 seconds, the balloon catheter should be removed from the system and replaced.

During pressure titration, the syringe is filled with up to 30 cc of D5W. Air is purged from the syringe and the syringe is connected to the balloon catheter. Up to 5 cc additional fluid may be used if needed, for a total of 35 cc. The above-mentioned fluid volumes are merely exemplary, and other fluid volume levels may be used and still fall within the scope of the present invention.

The depth of the uterus may be measured. Appropriate sterile techniques are preferably used for cervical/vaginal preparation, and the cervix may be dilated to 5 mm if necessary. If a perforation of the uterus is suspected, appropriate diagnostic measures are desirably performed to evaluate for perforation before proceeding. If perforation cannot be ruled out, the procedure is preferably abandoned. After determining the depth of the uterus (e.g. using uterus sounding techniques), dilating the uterus if necessary, and wetting the balloon with D5W, the balloon catheter may be slowly inserted into the uterus until the distal tip is touching the fundus. The operator preferably ensures that the depth indicated by the markings on the catheter is consistent with previous sound measurements. A tenaculum may be used to hold the cervix, if necessary.

The operator should not use excessive force during insertion, as such force may cause the balloon to tear or the catheter to perforate the uterine wall. If a perforation is suspected, the operator should preferably perform appropriate diagnostic measures to evaluate for perforation before proceeding. If perforation cannot be ruled out, the operator may abandon the procedure.

The fluid fill valve may be pressed to fill the balloon slowly to a pressure of about 160-180 mmHg using 2-35 cc of D5W. The fluid fill valve may be released to allow the pressure to stabilize. An operator should preferably not allow the pressure to exceed 200 mmHg during titration. Small volumes of fluid may be added incrementally to achieve a stable pressure, which is defined as no fluctuations greater than ±10 mmHg of 160-180 mmHg for a minimum of 30seconds. The pressure of the balloon against the uterine wall often precipitates uterine contraction, thereby temporarily increasing the pressure reading. If pressure cannot be stabilized at 160-180 mmHg for 30-45 seconds with up to 35 cc of fluid, this may indicate uterine perforation. An operator may remove the fluid and then remove the balloon catheter. If a balloon leak is present, the catheter may be replaced and the procedure continued. If no balloon leak is found, the procedure should preferably be aborted.

Activating heater. Once the heater is activated, the pressure may initially rise about 10-20 mmHg. The pressure may then drop slowly for the remainder of the procedure. The ending balloon pressure may be as low as approximately 100 mmHg, and is typically between 120-150 mmHg. It is recommended that for very small uteri, pressure titration should occur towards the lower end of the range (i.e. use a minimum amount of fluid to reach 160 mmHg). This will reduce the potential for increase of pressure during the thermal treatment that might result in overpressure and system shutdown. Care should be taken to insure the device is properly positioned in the uterine cavity. Positioning the device in an incorrect passage may allow the balloon to reach operating pressure with a small amount of fluid. This may be misinterpreted as being a small uterine cavity.

An operator should preferably ensure that the balloon is not over-pressurized during titration. The total fluid volume needed to achieve optimal balloon volume depends on the potential volume of the uterine cavity and is typically 6-20 cc at >160 mmHg (at start) and may be as great as 35 cc. If appropriate pressure levels cannot be reached with up to 35 cc of fluid, the balloon catheter should be removed and checked for uterine perforation and/or a balloon catheter leak. A defective balloon catheter may be replaced, if necessary.

At the beginning of the treatment, the message display preferably alternates back and forth between the following messages: READY—PRESS START and STABILIZE START—PRESSURE >150 mmHg. When a steady pressure of 160-180 mmHg is maintained, the START button on the controller is pressed to activate the heater. Fluid should not be added once the heater is activated, as this could create (or exacerbate if already present) a uterine wall defect such as a perforation. The balloon catheter is preferably held immobile and centered in the uterine cavity during the procedure (with the valve oriented upwards). Failure to hold the balloon catheter immobile during the procedure may result in catheter failure. The catheter should be held so that it does not rest on the vaginal wall during treatment and cool down periods to prevent possible burns. An operator should preferably ensure that the balloon catheter is centered in the uterus to minimize potential overheat error codes during the treatment process. Prior to activating the heater, an operator should ensure that fluid is on all sides of the catheter tip.

After the start button is pressed, the controller preferably activates the heater assembly to achieve a treatment temperature of 87° C. (188° F.) within 4 minutes. In one embodiment, the treatment temperature may be 81° C. or any other temperature used by those skilled in the art for endometrial ablation procedures. The preheat cycle may take up to 4 minutes for larger uteri, but is usually 15-45 seconds. The message display will read: PREHEATING TO 87° C. If the treatment temperature of 87° C. is not reached within 4 minutes, the controller will terminate the procedure by removing the fluid and then removing the catheter. During treatment and in case of emergency, the STOP button may be pressed to terminate the procedure. The stop button will power down the heater. The heater function may only be resumed by turning the unit off and restarting.

At the start of the procedure, the message display will show the following: THERAPY CYCLE—CYCLE 87° C., 8 MIN. Once 87° C. is reached, an audible tone will indicate the automatic activation of the 8-minute therapy cycle. The time elapsed will be shown on the "THERAPY TIME" display. After the preheat cycle is completed the time resets to 0:00.

The displayed time represents the exact therapy cycle time. Pressure may rise slightly with initial heating. It is common to then see the pressure fall gradually during the procedure. If the pressure reaches 200 mmHg, an alarm will sound. If the pressure exceeds 210 mmHg for more than 2 seconds, the controller will terminate the procedure. The procedure may be restarted with a lower starting pressure to complete an 8-minute therapy. A rapid drop in pressure or a failure to maintain pressure may be the result of a catheter leak or uterine perforation. After sufficient cooling, the fluid should be removed and then the balloon catheter should be removed to abort the procedure. A work-up for perforation should be considered prior to discharge. Additional fluid should never be added during a therapy cycle as this could create (or exacerbate if already present) a uterine wall defect such as a perforation.

When the treatment cycle is completed, the message display will alternate between the following messages: THERAPY COMPLETE and COOLING DOWN PLEASE WAIT. The controller automatically terminates the heater at the end of the treatment cycle and an audible alarm will sound.

Post Treatment. The cool down cycle takes 30 seconds. When the cycle is completed, the message display will read: THERAPY & COOL DOWN COMPLETED then REMOVE FLUID—REMOVE CATHETER. The fluid may be removed by drawing back on the syringe plunger while depressing the fluid fill valve. After all of the fluid is removed from the balloon, the balloon catheter may be removed from the uterus. The operator will preferably check that the entire fluid volume has been withdrawn. The cartridge may be disconnected from the controller. The catheter is preferably discarded. The power is preferably turned off before beginning another procedure. If the controller is left on without use for 8 hours, the controller may freeze and display the following message: MAX TIME EXPIRED—TURN POWER OFF.

Although particular embodiments of the present invention have been illustrated and described herein, various modifications may be made without departing from the spirit and scope of the invention, and other and further embodiments of the invention may be devised without departing from the basic scope thereof. Accordingly, the above disclosure is not intended to limit the scope of the invention, which is defined by the appended claims.

What is claimed is:
1. A system for treating uterine disorders comprising:
 a balloon catheter including a cannula having a proximal end and a distal end;
 an inflatable balloon secured over the distal end of said cannula;
 a heating assembly coupled with the distal end of said cannula and disposed inside said inflatable balloon, wherein said heating assembly comprises an elongated tube having a proximal end, a distal end, an outer wall extending between the proximal and distal ends, at least one fluid inlet adjacent the proximal end of said elongated tube and a fluid outlet located at a distal-most end of said elongated tube;
 an impeller disposed inside said heating assembly; and
 a cap inserted into said fluid outlet at the distal-most end of said elongated tube, said cap having an opening extending therethrough, wherein said elongated tube has a longitudinal axis and said fluid outlet located at the distal-most end of said elongated tube and said cap opening are aligned with the longitudinal axis for discharging fluid from the distal-most end of said elongated tube along an axis that is parallel to the longitudinal axis of said elongated tube.

2. The system as claimed in claim 1, wherein the total area of said at least one fluid inlet extending through said outer wall is at least equal to the total area of said fluid outlet located at the distal-most end of said elongated tube.

3. The system as claimed in claim 2, wherein said elongated tube is an elongated heating tube having at least one heating film overlying said outer wall, and wherein said cap is located completely inside said inflatable balloon.

4. The system as claimed in claim 2, wherein said impeller is rotatable for drawing fluid through said at least one fluid inlet and into said elongated tube for heating said fluid.

5. The system as claimed in claim 4, wherein said at least one fluid inlet is located adjacent the proximal end of said elongated tube, and wherein said rotatable impeller is adapted to discharge the fluid through said fluid outlet located at the distal end of said elongated tube so as to circulate the fluid throughout said inflatable balloon.

6. The system as claimed in claim 2, wherein said cannula comprises a lumen extending between the proximal and distal ends thereof for introducing a fluid into said inflatable balloon.

7. The system as claimed in claim 1, further comprising a drive shaft extending through said cannula that is coupled with said impeller for rotating said impeller.

8. The system as claimed in claim 7, wherein said drive shaft has a distal end that extends beyond a distal end of said impeller and wherein said cap is not connected with said inflatable balloon and covers the distal end of said drive shaft for spacing said impeller drive shaft and said inflatable balloon.

9. The system as claimed in claim 8, wherein said cap is insertable into said fluid outlet at the distal-most end of said elongated tube.

10. The system as claimed in claim 1, further comprising one or more conductive leads extending through said cannula and being coupled with said heating assembly.

11. The system as claimed in claim 1, wherein said balloon catheter further comprises a handle assembly secured to the proximal end of said cannula, said handle assembly including at least one element for controlling operation of said system.

12. The system as claimed in claim 6, further comprising a pressure monitor in communication with said lumen for monitoring fluid pressure inside said inflatable balloon.

13. The system as claimed in claim 12, further comprising a system controller for controlling operation of said system, said system controller including a microprocessor for running endometrial ablation procedures with a pressure monitoring subroutine, and a timer subroutine.

14. A system for treating uterine disorders comprising:
a balloon catheter including a cannula having a proximal end, a distal end, and a lumen extending between the proximal and distal ends of said cannula;
an inflatable balloon secured to the distal end of said cannula;
an elongated heating tube coupled with the distal end of said cannula and being disposed within said inflatable balloon, said elongated heating tube having at least one fluid inlet extending though an outer wall of said elongated heating tube and a fluid outlet located at a distal-most end of said elongated heating tube;
an impeller disposed inside said elongated heating tube; and
a cap inserted into said fluid outlet at the distal-most end of said elongated heating tube, said cap having an opening extending therethrough, wherein said elongated heating tube has a longitudinal axis and said fluid outlet and said cap opening are aligned with the longitudinal axis for discharging fluid from the distal-most end of said elongated heating tube along an axis that is parallel to the longitudinal axis of said elongated heating tube.

15. The system as claimed in claim 14, wherein said impeller is rotatable for drawing fluid through said at least one fluid inlet and into said elongated heating tube for transferring heat from said elongated heating tube to said fluid, and for discharging said heated fluid from said fluid outlet for circulating said heated fluid throughout said inflatable balloon.

16. The system as claimed in claim 15, wherein said cap covers said fluid outlet at the distal end of said elongated heating tube and is located completely inside said inflatable balloon for spacing said impeller from said inflatable balloon.

17. The system as claimed in claim 14, wherein said at least one fluid inlet is located adjacent a proximal end of said elongated heating tube, said system further comprising a heating film covering said elongated heating tube for transferring heat to fluid passing between the proximal and distal ends of said elongated heating tube.

18. The system as claimed in claim 14, further comprising a controller connected with said balloon catheter for controlling the temperature of said elongated heating tube, controlling rotation of said impeller, and including a pressure monitor for monitoring and controlling fluid pressure within said inflatable balloon.

19. The system as claimed in claim 14, wherein said elongated heating tube completely surrounds said impeller and extends distally beyond a distal end of said impeller.

20. A system for treating uterine disorders comprising:
a balloon catheter including a cannula having a proximal end and a distal end;
an inflatable balloon secured to the distal end of said cannula;
a heating assembly coupled with said cannula and being disposed within said inflatable balloon, said heating assembly comprising an elongated tube having a fluid inlet adjacent a proximal end thereof and a fluid outlet at a distal-most end thereof;
an impeller disposed inside said elongated tube of said heating assembly, wherein said impeller is rotatable for drawing fluid through said fluid inlet and into said heating assembly, directing said fluid inside said heating assembly from the proximal end to the distal end thereof, and discharging said fluid from said heating assembly through said fluid outlet for circulating said fluid within said inflatable balloon;
a cap inserted into said fluid outlet at the distal-most end of said elongated tube, said cap having an opening extending therethrough, wherein said elongated tube has a longitudinal axis and said fluid outlet and said cap opening are aligned with the longitudinal axis of said elongated tube for discharging fluid from the distal-most end of said elongated tube of said heating assembly along an axis that is parallel to the longitudinal axis of said elongated tube; and
a system controller for controlling the pressure level of said fluid inside said balloon, controlling the temperature level of said fluid inside said balloon, and controlling the length of an endometrial ablation procedure.

* * * * *